(12) United States Patent
Junio (10) Patent No.: US 12,109,075 B2
(45) Date of Patent: Oct. 8, 2024

(54) SYSTEMS AND METHODS FOR GENERATING A CORRECTED IMAGE

(71) Applicant: Mazor Robotics Ltd., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 274 days.

(21) Appl. No.: 17/464,356

(22) Filed: Sep. 1, 2021

(65) Prior Publication Data
US 2022/0079704 A1    Mar. 17, 2022

Related U.S. Application Data (60) Provisional application No. 63/078,751, filed on Sep. 15, 2020.

(51) Int. Cl.
*A61B 34/30* (2016.01)
*A61B 34/00* (2016.01)
*A61B 90/00* (2016.01)

(52) U.S. Cl.
CPC ............ *A61B 90/361* (2016.02); *A61B 34/70* (2016.02); *A61B 90/37* (2016.02); *A61B 2090/363* (2016.02); *A61B 2090/376* (2016.02)

(58) Field of Classification Search
CPC ......... A61B 34/00; A61B 34/30; A61B 34/70; A61B 90/00; A61B 90/37; A61B 90/361; A61B 19/201; A61B 19/203; A61B 19/5244
See application file for complete search history.

(56) References Cited

U.S. PATENT DOCUMENTS

| 7,369,695 B2 | 5/2008 | Zettel et al. |
| 7,548,604 B2 | 6/2009 | De Man et al. |
| 7,734,119 B2 | 6/2010 | Cheryauka et al. |

(Continued)

FOREIGN PATENT DOCUMENTS

| CN | 103440636 | 8/2016 |
| CN | 104545962 | 8/2017 |

(Continued)

OTHER PUBLICATIONS

International Search Report and Written Opinion for International (PCT) Patent Application No. PCT/IL2021/051103, dated Jan. 7, 2022, 12 pages.

(Continued)

*Primary Examiner* — Vi X Nguyen
(74) *Attorney, Agent, or Firm* — Sheridan Ross P.C.

(57) ABSTRACT

A system and method for generating a corrected image is provided. A plurality of poses for an imaging device may be calculated based on information about an object within a patient's anatomy. An image may be received from the imaging device at each pose of the plurality of poses to yield an image set. Each image may depict at least a portion of an anatomical element of the patient and an object. A set of saturated areas in which the object has caused saturated attenuation, and a set of unsaturated areas in which the object has not caused saturated attenuation may be identified in the images of the image set. A corrected image may be generated by combining data from the set of unsaturated areas, the corrected image depicting the anatomical feature with fewer than all of the saturated areas in the set of saturated areas.

10 Claims, 4 Drawing Sheets

(56) References Cited

U.S. PATENT DOCUMENTS

| | | |
|---|---|---|
| 8,280,135 B2 | 10/2012 | McCollough et al. |
| 8,503,750 B2 | 8/2013 | Benson et al. |
| 8,891,885 B2 | 11/2014 | Kachelriess et al. |
| 9,202,296 B2 | 12/2015 | Yang et al. |
| 9,235,908 B2 | 1/2016 | Jain et al. |
| 9,349,198 B2 | 5/2016 | Claus et al. |
| 9,514,549 B2 | 12/2016 | Kim et al. |
| 9,737,235 B2 | 8/2017 | Hartmann |
| 10,191,615 B2 | 1/2019 | Helm et al. |
| 10,366,472 B2 * | 7/2019 | Lelescu ............... H04N 13/111 |
| 10,453,198 B2 | 10/2019 | Manhart |
| 2009/0074278 A1 | 3/2009 | Beaulieu et al. |
| 2011/0007956 A1 | 1/2011 | Meyer et al. |
| 2017/0079727 A1 * | 3/2017 | Crawford ........... A61B 17/1757 |
| 2018/0217734 A1 | 8/2018 | Koenig et al. |
| 2019/0244420 A1 | 8/2019 | Alexandroni et al. |
| 2019/0311505 A1 | 10/2019 | Helm et al. |
| 2019/0325621 A1 | 10/2019 | Wang et al. |
| 2019/0374187 A1 | 12/2019 | Manhart |
| 2019/0378310 A1 | 12/2019 | Schildkraut et al. |
| 2020/0034969 A1 | 1/2020 | Isaacs et al. |

FOREIGN PATENT DOCUMENTS

| | | |
|---|---|---|
| CN | 105286902 | 1/2018 |
| EP | 2806801 | 11/2017 |
| JP | 2011-206367 | 10/2011 |
| KR | 10-1982941 | 8/2019 |
| WO | WO 2019/051209 | 3/2019 |
| WO | WO 2019/145149 | 8/2019 |
| WO | WO 2019/173452 | 9/2019 |
| WO | WO 2019/197531 | 10/2019 |

OTHER PUBLICATIONS

Chen et al. "CT Metal Artifact Reduction Method Based on Improved Image Segmentation and Sinogram In-Painting," Mathematical Problems in Engineering, 2012, vol. 2012, Article ID 786281, 19 pages.

Ghani et al. "Fast Enhanced CT Metal Artifact Reduction using Data Domain Deep Learning," arXiv, Aug. 2019, 1904.04691v3, 23 pages.

Gjesteby et al. "Metal Artifact Reduction in CT: Where Are We After Four Decades?" IEEE Access, 2016, vol. 4, pp. 5826-5849.

Katsura et al. "Current and Novel Techniques for Metal Artifact Reduction at CT: Practical Guide for Radiologists," RadioGraphics, Mar.-Apr. 2018, vol. 38, No. 2, pp. 450-461.

Nam et al. "A metal artifact reduction algorithm in CT using multiple prior images by recursive active contour segmentation," PLOS One, Jun. 2017, vol. 12, No. 6, article e0179022, 21 pages.

Park et al. "Machine-learning-based nonlinear decomposition of CT images for metal artifact reduction," arXiv, Aug. 2017, 1708. 00244v1, 8 pages.

Peng et al. "Gaussian diffusion sinogram inpainting for X-ray CT metal artifact reduction," BioMedical Engineering OnLine, 2017, vol. 16, Article 1, 17 pages.

Yu et al. "A segmentation-based method for metal artifact reduction," Academic Radiology, Apr. 2007, vol. 14, No. 4, pp. 495-504.

Zhang et al. "Metal artifact reduction in x-ray computed tomography (CT) by constrained optimization," Medical Physics, Feb. 2011, vol. 38, No. 2, pp. 701-711.

* cited by examiner

FIG. 4 sium # SYSTEMS AND METHODS FOR GENERATING A CORRECTED IMAGE

CROSS REFERENCE TO RELATED APPLICATIONS

This application claims the benefit of U.S. Provisional Application No. 63/078,751, filed on Sep. 15, 2020, and entitled "Systems and Methods for Generating a Corrected Image", which application is incorporated herein by reference in its entirety.

FIELD

The present technology is related generally to image generation, and more particularly, to generating a corrected image void of saturated attenuation caused by at least one object in an image sensor field view.

BACKGROUND

Registration using X-ray based images relies on identifying anatomical elements of a patient anatomy in X-ray images. These anatomical elements may be identified based on different levels of attenuation in the X-ray image corresponding to different anatomical elements and associated thicknesses. Metals, such as those used in medical devices, also cause attenuation in the image and will appear in the image along with the anatomical elements.

SUMMARY

Example Aspects of the Present Disclosure Include:

A method for generating a corrected image according to at least one embodiment of the present disclosure comprises: calculating a plurality of poses for an imaging device based on information about an object within a patient's anatomy that saturates attenuation in an image of the patient's anatomy; receiving an image from the imaging device at each pose of the plurality of poses to yield an image set, each image depicting at least a portion of an anatomical element of the patient and an object; identifying, in the images of the image set, a set of saturated areas in which the object has caused saturated attenuation, and a set of unsaturated areas in which the object has not caused saturated attenuation; and generating a corrected image by combining data from the set of unsaturated areas, the corrected image depicting the anatomical feature with fewer than all of the saturated areas in the set of saturated areas.

Any of the aspects herein, further comprising receiving a surgical plan having the information.

Any of the aspects herein, wherein calculating the plurality of poses for the imaging device includes calculating movements of a robotic arm holding the imaging device, the robotic arm having at least five degrees of freedom of movement.

Any of the aspects herein, wherein the imaging device utilizes X-rays.

Any of the aspects herein, wherein identifying the set of saturated areas and the set of unsaturated areas uses feature recognition, machine learning, or thresholding-based algorithms.

Any of the aspects herein, wherein the information includes at least one dimension of the object.

Any of the aspects herein, wherein generating the corrected image is further based on the pose corresponding to each image of the image set.

Any of the aspects herein, wherein the object comprises a plurality of objects.

Any of the aspects herein, wherein the plurality of poses is calculated to obtain an unobstructed view of each portion of the anatomical element in the corrected image.

A method for generating a corrected image according to at least one embodiment of the present disclosure comprises: receiving an image set from an imaging device, each image depicting at least a portion of an anatomical element of the patient and an object; identifying, in the images of the image set, a set of saturated areas in which the object has caused saturated attenuation, and a set of unsaturated areas in which the object has not caused saturated attenuation, wherein at least a portion of the anatomical element is within at least one saturated area of the set of saturated areas and at least one unsaturated area of the set of unsaturated areas; and generating a corrected image by combining data from the set of unsaturated areas, the corrected image depicting the portion of the anatomical element from the at least one unsaturated area.

Any of the aspects herein, further comprising determining a pose of the object and/or the anatomical element in the image based on the fiducial marker.

Any of the aspects herein, further comprising determining a pose of the imaging device for each image based on a fiducial marker, and wherein the corrected image is generated based in part on the corresponding pose of each image.

Any of the aspects herein, further comprising receiving a surgical plan having information about the object.

Any of the aspects herein, wherein the robotic arm has at least five degrees of freedom of movement.

Any of the aspects herein, wherein the information includes at least one dimension of the at least one object.

Any of the aspects herein, wherein the plurality of poses is calculated to obtain an unobstructed view of each portion of the anatomical element.

Any of the aspects herein, wherein identifying the set of saturated areas and the set of unsaturated areas comprises using at least one of a feature recognition, machine learning, or thresholding-based algorithm.

Any of the aspects herein, wherein the object is a metal object.

Any of the aspects herein, wherein the object comprises a plurality of objects.

A system for generating a corrected image according to at least one embodiment of the present disclosure comprises: at least one imaging device; a plurality of robotic arms, at least one arm of the plurality of robotic arms configured to hold the at least one imaging device; at least one processor; and at least one memory storing instructions for execution by the at least one processor that, when executed, cause the at least one processor to: calculate one or more poses for an imaging device based on information about at least one object and at least one anatomical element, receive one or more images from the imaging device at each pose of the one or more poses, the one or more images depicting at least a portion of the at least one anatomical element and the at least one object, identify a first set of areas in each image of the one or more images in which the at least one object has affected attenuation and a second set of areas in each image of the one or more images in which the at least one object has not affected attenuation, and generate a compound image based on combining the second set of areas in each image of the one or more images, the compound image depicting the anatomical feature with fewer than all of the first set of areas.

Any of the aspects herein, wherein the robotic arm has at least five degrees of freedom of movement.

Any of the aspects herein, wherein the memory stores additional instructions for execution by the at least one processor that, when executed, further cause the at least one processor to: receive a surgical plan comprising the information.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10x Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Use of titanium interbodies and other metal implants in spinal procedures within the surgical field raises a challenge during CT-fluoroscopy registrations or procedures where X-ray images are taken, such as during spinal procedures. Metal tends to "obscure" bony anatomy positioned in the same X-ray lines due to a saturation in the attenuation. This saturation may cause loss of anatomy in the image that may reduce a chance of a successful and accurate registration. Further, in cases where image registration is performed, the presence of metal in the X-ray image (where the metal was not present when a preoperative patient image was initially taken) can prevent registration of the images and therefore reduce or eliminate use of robots in such cases.

Embodiments of the present disclosure comprise taking several 2D X-ray images in a synchronized manner, such as taking the images in a pattern by an imaging device held by a robot. Multiple 2D X-ray images (as few as two) may be taken (albeit from different perspectives) of the portion of the anatomy that has the metal object(s) therein. The metal part(s) may be identified in the anatomy based on thresholding or machine-learning-based algorithms. The changes in attenuation caused by the metal part(s) may be combined based on comparisons between the portions of the images that depict the same anatomical feature(s). For example, where different parts of an end plate are "covered" by a metal implant that obscures the end plate in different images, the information gathered from the different images (each with a unique point of view) may be combined and incorporated into a single, corrected image. The end result is a metal-deducted image that reduces or minimizes, and in some cases, avoids, the anatomical loss of information due to the metal implant(s) obscuring the anatomy in specific images.

As described more fully below, methods and systems for generating a corrected image according to at least some embodiments of the present disclosure may beneficially provide a corrected metal-deducted image (e.g., an image without substantial attenuation saturation caused by metal objects in the image sensor field view) with sufficient information about a patient anatomy for a successful registration. Whether attenuation saturation is substantial may depend, for example, on whether the attenuation saturation prevents registration of the image. For example, an image with substantial attenuation saturation may have insufficient information about the patient anatomy for a successful registration, whereas an image without substantial attenuation saturation may have sufficient information about the patient anatomy for a successful registration. Also, the methods and systems described herein may use a robot to hold and move the imaging device to allow for imaging of the patient anatomy from any pose. Images obtained from the various angles can show the patient anatomy in different unobstructed views (or in different views that each have a different obstructed portion).

Figure 1:
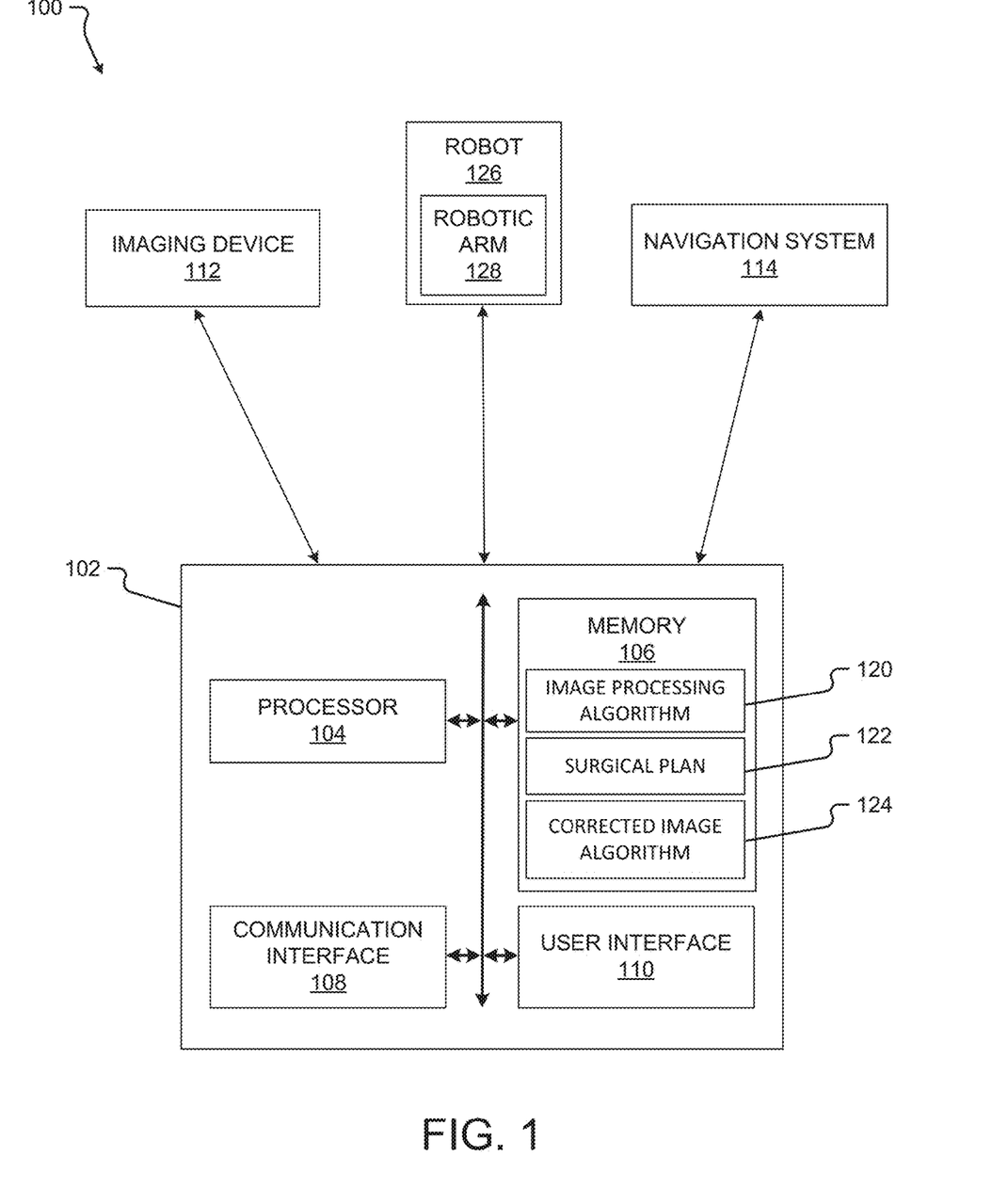
FIG. 1 is a block diagram of a system according to at least one embodiment of the present disclosure.

Turning first to FIG. 1, a block diagram of a system 100 according to at least one embodiment of the present disclosure is shown. The system 100 may be used to process image data; execute a corrected image algorithm 124 and/or an image processing algorithm 120; and/or carry out other aspects of one or more of the methods disclosed herein. The system 100 comprises a computing device 102, one or more imaging devices 112, a navigation system 114, and/or a robot 126. Systems according to other embodiments of the present disclosure may comprise more or fewer components than the system 100. For example, the system 100 may not include the navigation system 114 and/or the robot 126.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 126, and/or the navigation system 114.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 and/or 400 described herein. The memory 106 may store, for example, one or more image processing algorithms 120, one or more corrected image algorithms 124, and/or one or more surgical plans 122. Such algorithms may, in some embodiments, be organized into one or more applications, modules, packages, layers, or engines. The algorithms may cause the processor 104 to manipulate data stored in the memory 106 and/or received from the imaging device 112, the robot 126, and/or the navigation system 114.

The computing device 102 may also comprise a communication interface 108. The communication interface 108 may be used for receiving image data or other information from an external source (such as the imaging device 112, the navigation system 114 and/or the robot 126), and/or for transmitting instructions, images, or other information to an external system or device (e.g., another computing device 102, the navigation system 114, the imaging device 112, and/or the robot 126). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding receiving a surgical plan having information about an object within a patient's anatomy that saturates attenuation in an image of the patient's anatomy; to receive a user selection or other user input regarding calculating a plurality of poses for an imaging device based on the information; to receive a user selection or other user input regarding receiving an image from the imaging device at each pose of the plurality of poses to yield an image set; to receive a user selection or other user input regarding identifying, in the images of the image set, a set of saturated areas in which the object has caused saturated attenuation, and/or a set of unsaturated areas in which the object has not caused saturated attenuation; to receive a user selection or other user input regarding generating a corrected image by data from the set of unsaturated areas, the corrected image depicting the anatomical feature with fewer than all of the set of saturated areas; and/or to display the set of images, the corrected image, and/or the surgical plan 122. In some embodiments, the user interface 110 may be useful to allow a surgeon or other user to modify the plan 122, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be capable of taking a 2D image or a 3D image to yield an image and/or image data. "Image data" as used herein refers to the data generated or captured by an imaging device, including in a machine-readable form, a graphical form, and in any other form. In various examples, the image data may comprise data corresponding to an anatomical feature of the patient or a portion thereof (e.g., a spinal region). The imaging device 112 may be or comprise, for example, a CT scanner, but may also be or comprise a fluoroscope, an ultrasound probe, an O-arm, a C-arm, a G-arm, any other device utilizing X-ray-based imaging, a magnetic resonance imaging (MM) scanner, an optical coherence tomography scanner, an endoscope, a telescope, a thermographic camera (e.g., an infrared camera), or any other imaging device suitable for obtaining images or image data corresponding to an anatomical feature of a patient.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, or other objects within the operating room or other room where a surgery takes place. In various embodiments, the navigation system 114 may be used to track a position of the imaging device 112 (or, more particularly, of a navigated reference marker attached, directly or indirectly, in fixed relation to the imaging device 112) and/or of the robot 126 (or, more particularly, of a navigated reference marker attached, directly or indirectly, in fixed relation to the robot 126). The navigation system 114 may include a display for displaying one or more images from an external source (e.g., the computing device 102, imaging device 112, or other source) or a video stream from the camera or other sensor of the navigation system 114.

In some embodiments, the navigation system 114 may be used to track movement of the robot 126 and may provide feedback regarding or confirmation of a position of the robot 126. For example, the navigation system 114 may indicate—audibly and/or visually via a display—that the robot 126 needs to be moved, automatically or manually, to a suggested robot pose. The navigation system 114 can monitor or track the robot 126 as the robot 126 is moved toward the suggested robot pose. The navigation system 114 can further indicate to or alert a user when the robot 126 has reached the suggested robot pose. In other embodiments, a user may view a display of the navigation system 114 while moving the robot 126 to the suggested robot pose, so as to ensure that the user moves the robot 126 to the correct pose. In some embodiments, the system 100 can operate without the use of navigation system 114.

The robot 126 may be any surgical robot or surgical robotic system. The robot 126 may be or comprise, for example, the Mazor X™ Stealth Edition robotic guidance system. The robot 126 may comprise one or more robotic arms 128. In some embodiments, the robotic arm 128 may comprise a plurality of robotic arms, though the robot 126 may comprise one robotic arm, two robotic arms, or more than two robotic arms. The robotic arm 128 may be used to selectively hold and/or operate one or more imaging devices 112, and/or any other tool or instrument. In some embodiments, the robotic arm 128 has at least five degrees of freedom. In other embodiments, the robotic arm 128 has at least six degrees of freedom. In yet other embodiments, the robotic arm 128 has fewer than five or greater than six degrees of freedom. The robotic arm 128 (and/or a base of the robot 126) may also have three dimensions of orientation. The combination of multiple degrees of freedom and multiple dimensions of orientation allows for the robotic arm 128 to move to any pose. In other words, the robotic arm 128 is not limited to a fixed area and can move in any direction. Further, in some embodiments, the robot 126 can move during a surgical procedure to position the robotic arm 128 (and thus, the imaging device 112) within reach of a pose.

Reference markers (e.g., navigation markers) may be placed on the robot 126, the robotic arm 128, the imaging device 112, and/or any other object in the surgical space. The reference markers may be tracked by the navigation system 114, and the results of the tracking may be used by the robot 126 and/or by an operator of the system 100 or any component thereof. As described above, in some embodiments, the navigation system 114 can be used to track other components of the system 100 (e.g., the imaging device 112) and the system 100 can operate without the use of the robot 126 (e.g., with the surgeon manually manipulating the imaging device 112).

Figure 2:
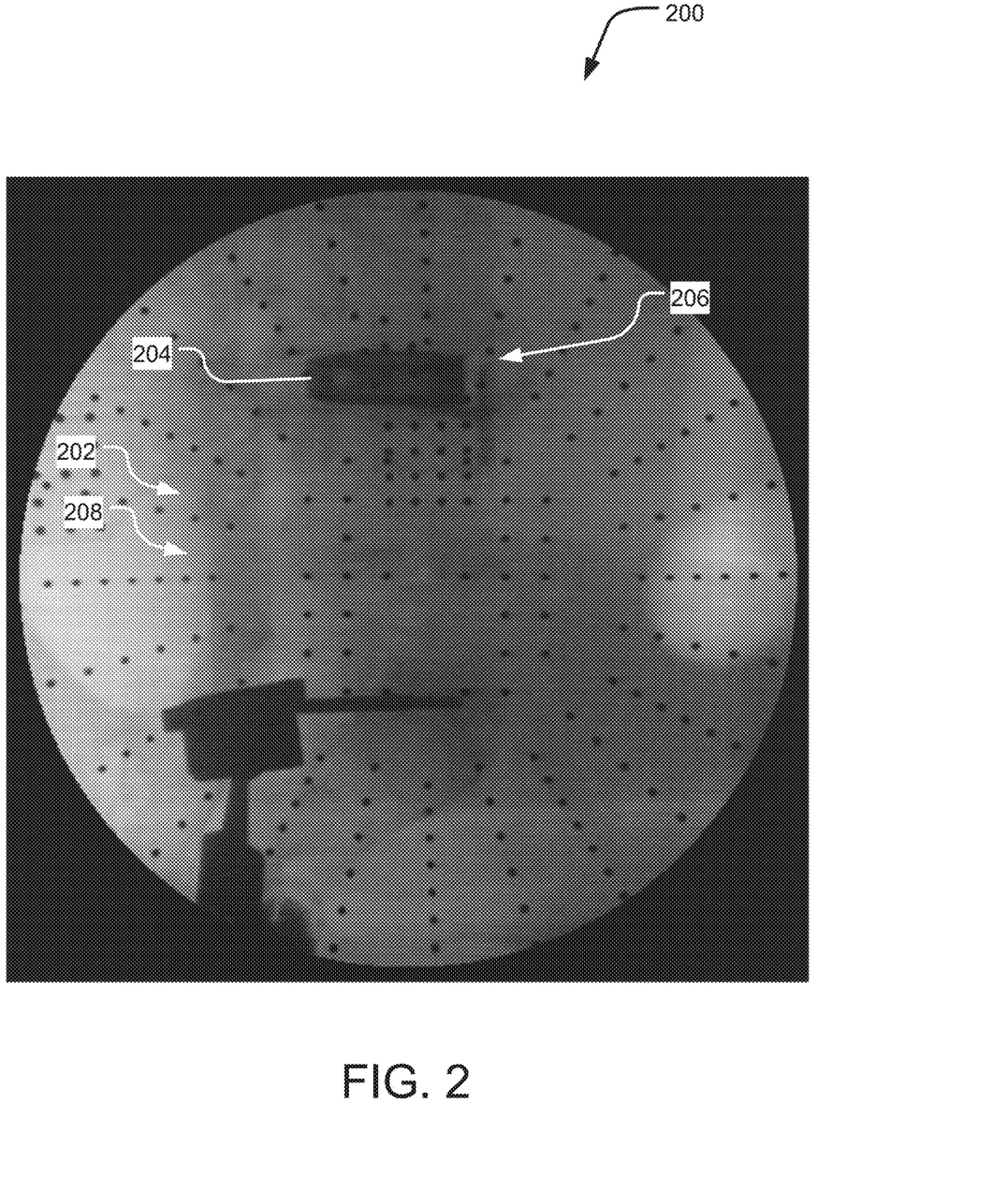
FIG. 2 is an X-ray image depicting an anatomical element and at least one object.

Turning to FIG. 2, an X-ray image 200 depicting a patient anatomy 202 and an object 204 is shown. The object 204 may be a metal object such as, for example, titanium, stainless steel, aluminum, or the like. In some embodiments, the object 204 may be fashioned of polyetheretherketone (PEEK) and may have, for example, one or more metal endcaps. Though one object is illustrated in FIG. 2, it will be appreciated that more than one object may be depicted in an X-ray image. For example, the image 200 may depict multiple screws.

As shown, the object 204 (or a portion thereof) causes a saturation in attenuation of the X-ray image 200. This is depicted as one or more saturated areas 206 having a brightness so great that details of the imaged anatomy/structure are not apparent. In contrast, the patient anatomy 202 affects attenuation, but does not saturate the image 200, resulting in one or more unsaturated areas 208 in which anatomical details are visible. The one or more saturated areas 206 may distort or hide details of the patient anatomy 202 surrounding and/or in proximity of the object 204. For example, as shown in the illustrated image 200, the area of the patient anatomy 202 behind the object 204 is obscured or hidden. As such, registration may be difficult to perform based on the image 200 alone when information about the patient anatomy that can be obtained from the image 200 is insufficient for registration.

However, as will be described in more detail below, an image taken from another angle may provide information about at least a portion of the patient anatomy that may no longer be obscured. For example, an image taken from a position rotated ninety degrees about a center axis of the patient anatomy 202 and the object 204 may provide information (e.g., one or more unsaturated areas 208) about the patient anatomy 202 behind the object 204. Thus, information about the patient anatomy 202 can be gathered from images taken from different angles, and such information from multiple images may then be combined to deduct or otherwise replace the object 204.

Figure 3:
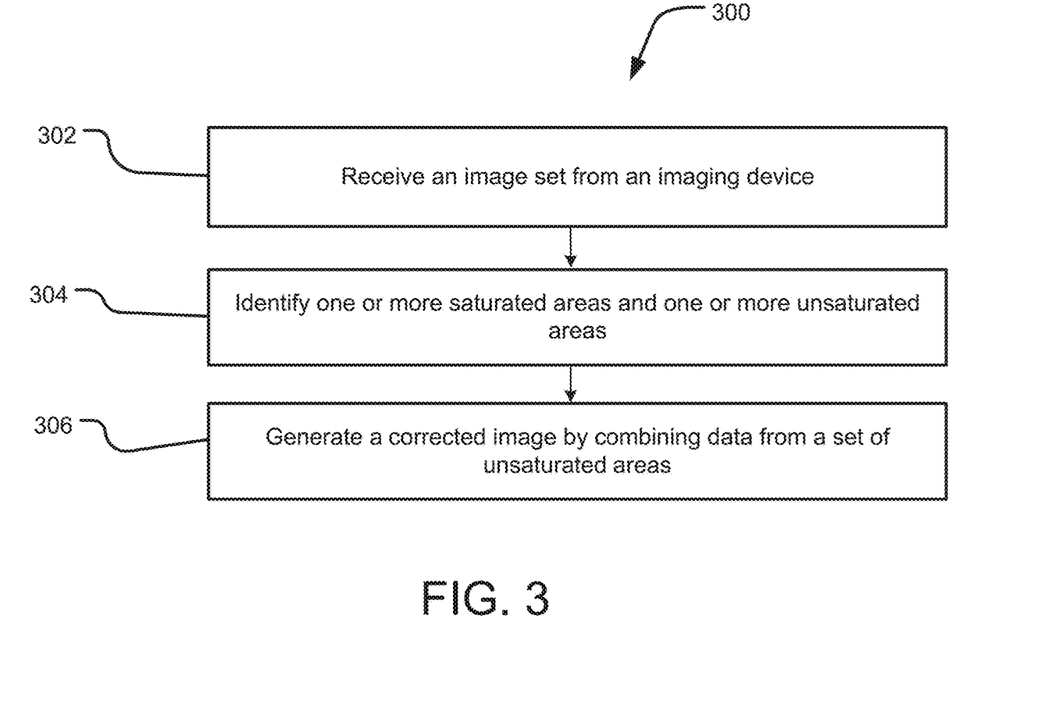
FIG. 3 is a flowchart of a method according to at least one embodiment of the present disclosure.

Turning now to FIG. 3, a method 300 for generating a corrected image may be executed in whole or in part, for example, on a computing device such as the computing device 102 or similar device, and may utilize one or more other components of the system 100 or similar components. One or more aspects of the method 300 may be performed by or with a surgical robot, a surgeon, or a combination of both using one or more imaging devices such as the imaging device 112.

The method 300 comprises receiving an image set from an imaging device such as the imaging device 112 (step 302). The imaging device may be any device utilizing X-ray-based imaging. The image set may comprise one or more 2D images, one or more 3D images, or a combination of one or more 2D images and one or more 3D images. In some embodiments, one imaging device may be used to obtain the image set. In other embodiments, multiple imaging devices may be used to obtain the image set. For example, a first imaging device may obtain a first one of the images independently of a second imaging device obtaining a second one of the images. In another example, at least a first one of the images may be obtained with a first imaging device and at least a second one of the images may be obtained with a second imaging device.

In other embodiments, the image set may be received via a user interface such as the user interface 110 and/or via a communication interface such as the communication interface 108 of a computing device such as the computing device 102, and may be stored in a memory such as the memory 106. The image set may also be generated by and/or uploaded to any other component of the system 100. In some embodiments, the image set may be indirectly received via any other component of the system 100 or a node of a network to which the system 100 is connected.

Each image of the image set may depict at least a portion of an object, such as the object 204, and an anatomical element of a patient. In some embodiments, each image may also depict at least a portion of a fiducial marker. The fiducial marker may be used by a navigation system such as the navigation system 114 to determine a pose (e.g., a position and an orientation) of the corresponding image device that obtained the image, or at least a pose of the object and/or the anatomical element in the image. In other embodiments, a pose of the corresponding image device may be obtained from a known pose of a robotic arm, such as the robotic arm 128, holding the imaging device.

Each image may be processed using an image processing algorithm such as the image processing algorithm 120 to identify the anatomical element and the object in the image. In some embodiments, feature recognition may be used to identify a feature of the anatomical element and/or of the object. For example, a contour of a vertebrae, femur, or other bone may be identified in the image. In other embodiments, the image processing algorithm may use artificial intelligence or machine learning to identify the anatomical element and/or the object. In such embodiments, a plurality of training images may be provided to a processor such as the processor 104, each training image annotated to include identifying information about an object and/or an anatomical element in the image. The processor, executed instructions stored in memory such as the memory 106 or in another memory, may analyze the images using a machine-learning algorithm and, based on the analysis, generate one or more image processing algorithms such as the image processing algorithms 120 for identifying anatomical elements and/or objects in an image.

The method 300 also comprises identifying one or more saturated areas such as the one or more saturated areas 206 and one or more unsaturated areas such as the one or more unsaturated areas 208 in each image of the image set (step 304). The one or more saturated areas correspond to areas of each image in which the object has caused saturated attenuation and the one or more unsaturated areas correspond to areas of each image in which the object has not caused saturated attenuation. In some embodiments, identifying the one or more saturated areas and the one or more unsaturated areas uses feature recognition, machine learning, or thresholding-based algorithms. For example, the set of saturated areas may be determined by setting a threshold of saturation based on a predetermined highest level of acceptable attenuation, and/or based on a highest level of attenuation identified in one or more images. In the same example, an area of the image is identified as a saturated area when an attenuation level in the image meets the threshold of saturation. In another example, sample images with known areas of saturation may be used to train a machine learning algorithm to identify a one or more saturated areas in a new image. In another example, feature recognition may be used to identify the object in each image.

The method 300 further comprises generating a corrected image by combining data from a set of unsaturated areas comprising the one or more unsaturated areas of each image in the image set (step 306). The corrected image may be generated using a corrected image algorithm such as the corrected image algorithm 124 to combine the data from the set of unsaturated areas. The corrected image may be based at least in part on a pose of the imaging device at the time of capture of each image, as determined from a fiducial marker, a known pose of the robotic arm, or otherwise. For example, one or more saturated areas of a first image of the image set may be matched or otherwise correlated to one or more unsaturated areas of a second image of the image set (e.g., using a known pose from which the first image and the second image were taken). In such examples, the second image depicts at least a portion of the one or more saturated areas of the first image as unsaturated. In the same example, the one or more unsaturated areas of the second image may be used to update or replace the one or more saturated areas in the first image, or the one or more unsaturated areas of each of the first image and the second image may be combined into a new image.

In some embodiments, the corrected image may be a three-dimensional (3D) model and the set of images may be two-dimensional (2D) images. In the same embodiments, the one or more unsaturated areas of each image may be combined into the 3D model such that the 3D model comprises fewer than all of the saturated areas caused by the object in the images, or otherwise reduces or diminishes the number and/or effect of such saturated areas in the model. In other words, where a portion of an anatomical element falls within an unsaturated area in a first image of the set of images and within a saturated area in a second image of the set of images, the portion of the 3D model corresponding to that portion of the anatomical element is generated based on data from or otherwise corresponding to the unsaturated area of the first image, rather than the saturated area from the second image. In other embodiments, the objects in a 3D model are replaced with alternative pixel data generated from a set of filtered 2D images, as described in U.S. Publication No. 2019/0244420, entitled "Imaging Reconstruction System and Method" and filed on Jan. 28, 2019, which is incorporated by reference in its entirety.

The method 300 may also comprise receiving a surgical plan such as the surgical plan 122. The surgical plan may be received via a user interface (e.g., the user interface 110) and/or a communication interface (e.g., the communication interface 108) of a computing device such as the computing device 102, and may be stored in a memory such as the memory 106 of the computing device 102. The surgical plan includes information about an object, such as the object 204, within a patient's anatomy that causes saturated attenuation in an image of the patient's anatomy. The information may include information about a position and/or orientation of the object. The information may also include at least one dimension of the object, which may be useful in identifying the one or more saturated areas in each image. The surgical plan may also include information about one or more planned movements of the imaging device held by the robotic arm. In some embodiments, the surgical plan includes a planned trajectory or path of one or more imaging devices to position the imaging device in each pose.

Figure 4:
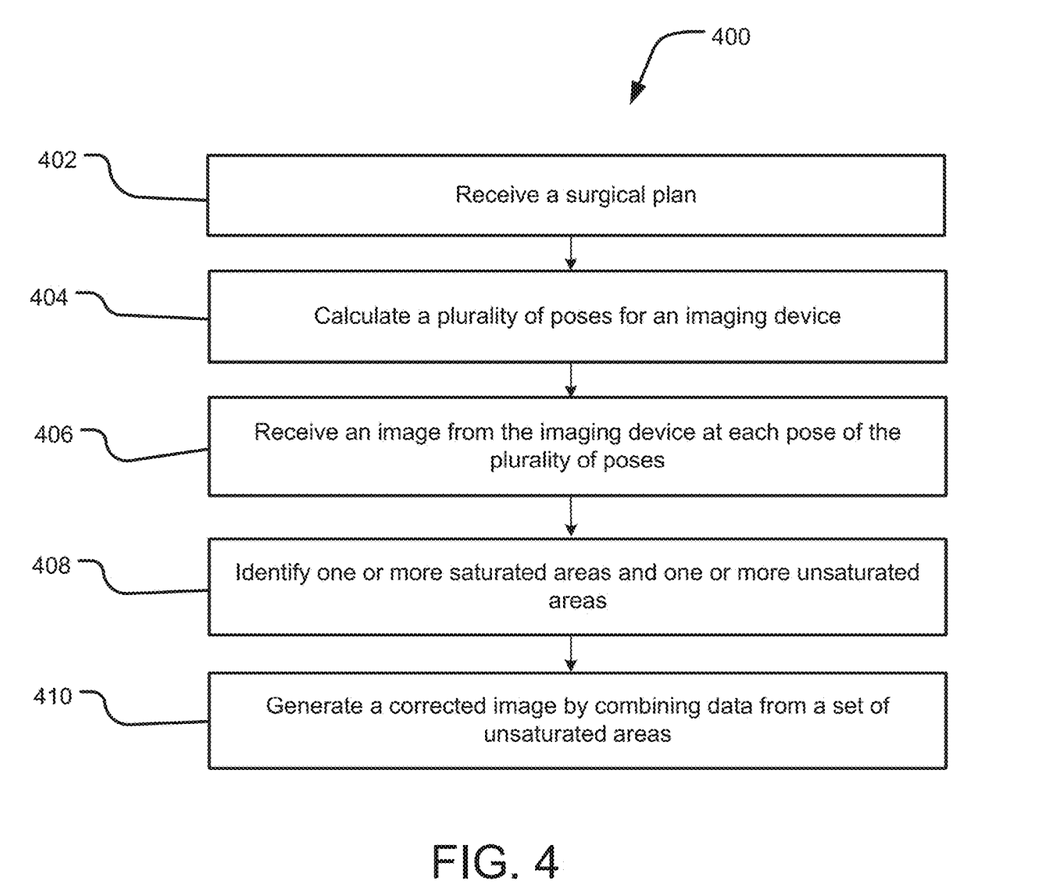
FIG. 4 is a flowchart of a method according to at least one embodiment of the present disclosure.

Turning now to FIG. 4, a method 400 for generating a corrected image may be executed in whole or in part, for example, on a computing device such as the computing device 102 or similar device, and may utilize one or more other components of the system 100 or similar components. One or more aspects of the method 400 may be performed by or with a surgical robot, a surgeon, or a combination of both using one or more imaging devices such as the imaging device 112.

The method 400 comprises receiving a surgical plan (step 402). The surgical plan may be received via a user interface (e.g., the user interface 110) and/or a communication interface (e.g., the communication interface 108) of a computing device such as the computing device 102, and may be stored in a memory such as the memory 106 of the computing device 102. The surgical plan includes information about an object, such as the object 204, within a patient's anatomy that causes saturated attenuation in an image of the patient's anatomy. The information may include information about a position and/or orientation of the object. The information may also include at least one dimension of the object, which may be useful in locating and identifying one or more saturated areas such as the one or more saturated areas 206 in each image. The surgical plan may also include information about one or more planned movements of the imaging device held by a robotic arm such as the robotic arm 128. In some embodiments, the surgical plan includes a planned trajectory of one or more imaging devices to position the imaging device in each pose.

The method 400 also comprises calculating a plurality of poses for the imaging device based on the information (step 404). In embodiments where the information includes the position and/or orientation of the object, the poses may be calculated to image the patient anatomy surrounding the object from various angles. For example, the plurality of poses may be calculated to obtain an unobstructed view of each portion of an anatomical element. In other words, the plurality of poses may be calculated such that each image obtains a view of at least a portion of the anatomical element in which the object is not obstructing the anatomical element from each respective pose.

Calculating the plurality of poses may also include calculating movements of a robotic arm such as the robotic arm 128 holding the imaging device. The robotic arm may have at least five degrees of freedom in some embodiments, though the robotic arm can have fewer than or greater than five degrees of freedom. The at least five degrees of freedom allow the robotic arm to move laterally, in an orbital movement about an area, or rotationally. Such movements provide for positioning of the imaging device in areas that may be difficult to reach as the robotic arm can move the imaging device in a unique path that can include a combination of movement types. For example, the robotic arm may follow a trajectory that moves the imaging device laterally, then rotationally.

The method 400 also comprises receiving an image set from an imaging device such as the imaging device 112 at each pose of the plurality of poses (step 406). The imaging device may be any device utilizing X-ray-based imaging. The image set may comprise one or more 2D images, one or more 3D images, or a combination of one or more 2D images and one or more 3D images. In some embodiments, one imaging device may be used to obtain the image set. In other embodiments, multiple imaging devices may be used to obtain the image set. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In other embodiments, multiple robotic arms may be used to hold the imaging device (in sequence) or multiple imaging devices (whether in parallel or in sequence) in different poses. In still other embodiments, a first imaging device may obtain an image at each pose of a first set of the one or more poses and a second imaging device may obtain another image at each pose of a second set of the one or more poses.

In other embodiments, the image set may be received via a user interface such as the user interface 110 and/or via a communication interface such as the communication interface 108 of a computing device such as the computing device 102, and may be stored in a memory such as the memory 106. The image set may also be generated by and/or uploaded to any other component of the system 100. In some embodiments, the image set may be indirectly received via any other component of the system 100 or a node of a network to which the system 100 is connected.

Each image of the image set may depict at least a portion of an object, such as the object 204 and at least a portion of an anatomical element of a patient. Each image may be processed using an image processing algorithm such as the imaging processing algorithm 120 to identify the anatomical element and the object in the image. In some embodiments, feature recognition may be used to identify a feature of the anatomical element and/or of the object. For example, a contour of a vertebrae or femur may be identified in the image. In other embodiments, the image processing algorithm may use artificial intelligence or machine learning to identify the anatomical element and/or the object.

Each image may be processed using an image processing algorithm such as the image processing algorithm 120 to identify the anatomical element and the object in the image. In some embodiments, feature recognition may be used to identify a feature of the anatomical element and/or of the object. For example, a contour of a vertebrae, femur, or other bone may be identified in the image. In other embodiments, the image processing algorithm may use artificial intelligence or machine learning to identify the anatomical element and/or the object. In such embodiments, a plurality of training images may be provided to a processor such as the processor 104, each training image annotated to include identifying information an object and/or an anatomical element in the image. The processor, executed instructions stored in memory such as the memory 106 or in another memory, may analyze the images using a machine-learning algorithm and, based on the analysis, generate one or more image processing algorithms such as the image processing algorithms 120 for identifying anatomical elements and/or objects in an image.

The method 400 also comprises identifying a one or more saturated areas such as the one or more saturated areas 206 and one or more unsaturated areas such as the one or more unsaturated areas 208 in each image of the image set (step 408). The one or more saturated areas correspond to areas of each image in which the object has caused saturated attenuation and the one or more unsaturated areas correspond to areas in which the object has not caused oversaturated attenuation. In some embodiments, identifying the one or more saturated areas and the one or more unsaturated areas uses feature recognition, machine learning, or thresholding-based algorithms. For example, the set of saturated areas may be determined by setting a threshold of saturation based on a predetermined highest level of acceptable attenuation, and/or based on a highest level of attenuation identified in one or more images. In the same example, an area of the image is identified as a saturated area when an attenuation level in the image meets the threshold of saturation. In another example, sample images with known areas of saturation may be used to train a machine learning algorithm to identify a one or more saturated areas in a new image. In another example, feature recognition may be used to identify the object in each image.

The method 400 further comprises generating a corrected image by combining data from a set of unsaturated areas comprising the one or more unsaturated areas of each image in the image set (step 410). The corrected image may be generated using a corrected image algorithm such as the corrected image algorithm 124 to combine the data from the set of unsaturated areas. The corrected image may be based at least in part on a pose of the imaging device at the time of capture of each image, as determined from a fiducial marker, a known pose of the robotic arm, or otherwise. For example, one or more saturated areas of a first image of the image set may be matched or otherwise correlated to one or more unsaturated areas of a second image of the image set (e.g., using a known pose from which the first image and the second image were taken). In such examples, the second image depicts at least a portion of the one or more saturated areas of the first image as unsaturated. In the same example, the one or more unsaturated areas of the second image may be used to update or replace the one or more saturated areas in the first image, or the one or more unsaturated areas of each of the first image and the second image may be combined into a new image.

In some embodiments, the corrected image may be a three-dimensional (3D) model and the set of images may be two-dimensional (2D) images. In the same embodiments, the one or more unsaturated areas of each image may be combined into the 3D model such that the 3D model comprises fewer than all of the saturated areas caused by the object in the images, or otherwise reduces or diminishes the number and/or effect of such saturated areas in the model. In other words, where a portion of an anatomical element falls within an unsaturated area in a first image of the set of images and within a saturated area in a second image of the set of images, the portion of the 3D model corresponding to that portion of the anatomical element is generated based on data from or otherwise corresponding to the unsaturated area of the first image, rather than the saturated area from the second image. In other embodiments, the objects in a 3D model are replaced with alternative pixel data generated from a set of filtered 2D images, as described in U.S. Publication No. 2019/0244420, entitled "Imaging Reconstruction System and Method" and filed on Jan. 28, 2019, which is incorporated by reference in its entirety.

Methods and systems for generating a corrected image according to at least some embodiments of the present disclosure beneficially provide a corrected, metal-deducted image to provide an image with sufficient information about a patient anatomy to enable successful registration. Further, use of a robot with the imaging device allows for imaging of the patient anatomy from any pose and thus, images from various angles that show the patient anatomy in different unobstructed views can be obtained.

As may be appreciated based on the foregoing disclosure, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the method 300 and 400). One or more steps of the methods described herein may be performed in an order other than the order in which they are described herein.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for generating a corrected image comprising:
calculating a plurality of poses for an imaging device based on information about an object within a patient's anatomy that saturates attenuation in an image of the patient's anatomy;
calculating one or more trajectories of a robotic arm orienting the imaging device based on the plurality of poses, wherein the robotic arm has at least five degrees of freedom of movement;
receiving an image from the imaging device at each pose of the plurality of poses to yield an image set, each image in the image set depicting at least a portion of an anatomical element of the patient and the object;
identifying, in the images of the image set, a set of saturated areas in which the object has caused saturated attenuation, and a set of unsaturated areas in which the object has not caused saturated attenuation; and
generating a corrected image by combining data from the set of unsaturated areas, the corrected image depicting the anatomical element with fewer than all of the saturated areas in the set of saturated areas.

2. The method of claim 1, further comprising receiving a surgical plan having the information.

3. The method of claim 1, wherein the imaging device utilizes X-rays.

4. The method of claim 1, wherein identifying the set of saturated areas and the set of unsaturated areas uses feature recognition, machine learning, or thresholding-based algorithms.

5. The method of claim 1, wherein the information includes at least one dimension of the object.

6. The method of claim 1, wherein generating the corrected image is further based on the pose corresponding to each image of the image set.

7. The method of claim 1, wherein the object comprises a plurality of objects.

8. The method of claim 1, wherein the plurality of poses is calculated to obtain an unobstructed view of each portion of the anatomical element in the corrected image.

9. A system for generating a corrected image comprising:
at least one imaging device;
a plurality of robotic arms, at least one arm of the plurality of robotic arms configured to hold the at least one imaging device;
at least one processor; and
at least one memory storing instructions for execution by the at least one processor that, when executed, cause the at least one processor to:
calculate one or more poses for the at least one imaging device based on information about at least one object and at least one anatomical element,
calculate one or more trajectories of the at least one robotic arm orienting the at least one imaging device based on the one or more poses, wherein the at least one robotic arm has at least five degrees of freedom of movement,
receive one or more images from the at least one imaging device at each pose of the one or more poses, the one or more images depicting at least a portion of the at least one anatomical element and the at least one object,
identify a first set of areas in each image of the one or more images in which the at least one object has affected attenuation and a second set of areas in each image of the one or more images in which the at least one object has not affected attenuation, and
generate a compound image based on combining the second set of areas in each image of the one or more images, the compound image depicting the at least one anatomical element with fewer than all of the first set of areas.

10. The system of claim 9, wherein the memory stores additional instructions for execution by the at least one processor that, when executed, further cause the at least one processor to:
receive a surgical plan comprising the information.

* * * * *